United States Patent
Hu et al.

(10) Patent No.: US 8,822,226 B2
(45) Date of Patent: Sep. 2, 2014

(54) METHOD FOR QUICK AND SIMULTANEOUS DETERMINATION OF 16 INORGANIC ANIONS AND ORGANIC ACIDS IN TOBACCO

(75) Inventors: Jing Hu, Guangdong (CN); Ruifeng Zhao, Guangdong (CN); Wenzhuang Shi, Guangdong (CN); Feng Li, Guangdong (CN); Rong Zhou, Guangdong (CN); Bing Han, Guangdong (CN)

(73) Assignee: China Tobacco Guangdong Industrial Co., Ltd., Guangdong (CN)

( * ) Notice: Subject to any disclaimer, the term of this patent is extended or adjusted under 35 U.S.C. 154(b) by 0 days.

(21) Appl. No.: 13/806,115

(22) PCT Filed: Dec. 7, 2011

(86) PCT No.: PCT/CN2011/083659
§ 371 (c)(1),
(2), (4) Date: Dec. 20, 2012

(87) PCT Pub. No.: WO2012/075950
PCT Pub. Date: Jun. 14, 2012

(65) Prior Publication Data
US 2013/0095571 A1      Apr. 18, 2013

(30) Foreign Application Priority Data
Dec. 8, 2010   (CN) .......................... 2010 1 0577905

(51) Int. Cl.
*G01N 33/00*     (2006.01)
*G01N 30/96*     (2006.01)
*G01N 30/88*     (2006.01)

(52) U.S. Cl.
CPC ...... *G01N 33/0098* (2013.01); *G01N 2030/884* (2013.01); *G01N 30/96* (2013.01)
USPC ....................................... 436/103

(58) Field of Classification Search
CPC ........................... G01N 33/0098; G01N 33/00
USPC .......................................................... 436/103
See application file for complete search history.

(56) References Cited

FOREIGN PATENT DOCUMENTS

| | | |
|---|---|---|
| CN | 101113972 A | 1/2008 |
| CN | 101131378 A | 2/2008 |
| CN | 102128885 A | 7/2011 |
| JP | 11-83827 A | 3/1999 |
| SU | 1555664 A1 | 4/1990 |

OTHER PUBLICATIONS

Zhang, Xia et al, Analysis of organic acids and inorganic anions in tobacco by ion chromatography and cluster analysis, Acta Tabacaria Sinica, Apr. 2009, pp. 13-18.*
English Translation of Analysis of organic acids and inorganic anions in tobacco by ion chromatography and cluster analysis.*

* cited by examiner

*Primary Examiner* — Christine T Mui
(74) *Attorney, Agent, or Firm* — Muncy, Geissler, Olds & Lowe, P.C.

(57) ABSTRACT

The present invention discloses a method for quick and simultaneous determination of 16 inorganic anions and organic acids in tobacco by ion chromatography The retention behavior of inorganic anions and organic acids on the anion exchange column was investigated using potassium hydroxide produced by EGC-II KOH eluent autogenerator as eluent. The optimized gradient elution condition was obtained. The samples were prepared through extraction, filtration and dilution before analysis. The separation was performed on an anion exchange column. The time of the gradient elution program was 50 mins. Under the optimized conditions, the calibration of peak area for all the analytes were linear in the ranges of $10^5$. The method in the present invention has the advantages of simplicity, rapidity and accuracy, and is able to simultaneously determine 16 inorganic anions and organic acids in tobacco by one single time of injection.

2 Claims, 2 Drawing Sheets

METHOD FOR QUICK AND SIMULTANEOUS DETERMINATION OF 16 INORGANIC ANIONS AND ORGANIC ACIDS IN TOBACCO

FIELD OF THE INVENTION

The present invention relates to the detection technology of tobacco industry. Specifically, the present invention relates and in particular, to detect the inorganic anions and organic acids in tobacco.

BACKGROUND OF THE INVENTION

The inorganic anions in tobacco such as $F^-$, $Cl^-$, $NO_2^-$, $Br^-$, $SO_4^-$, $NO_3^-$ etc. have significant effects on the physiology of tobacco and the quality of tobacco products. If the tobacco leaf has high content of nitrate salts, the fume will have high content of compounds with nitro groups. Compounds with nitro and nitroso groups can cause the cancerations or toxications of animals; sulfur and chlorine have negative effects on the combustibility of cigarette; bromine can partially substitute for chlorine. Therefore, inorganic anions such as nitrate ions, nitrite ions, chloride ions etc., are important items in tobacco determinations. The organic acids in tobacco are intermediates of the tricarboxylic acid cycle in carbohydrate metabolism, which are closely related to the growth of tobacco. The organic acids in tobacco are divided into two categories, volatile and non-volatile. Volatile organic acids contain acetic acid, formic acid, propionic acid and the like. Volatile organic acids could generate fragrance which have been found to be good for tobacco. Non-volatile organic acids mainly contain binary acids and trinary acids such as citric acid, malic acid, oxalic acid and so on, and they make up more than half of the total content of organic acids in tobacco. Most of the organic acids are in the form of salts, containing nicotine, ammonia and inorganic ions such as calcium ion, potassium ion and sodium ion. The maturity of tobacco is related to the ratio of oxalic acid to citric acid and the higher the better. The organic acids such as malic acid, citric acid, oxalic acid, etc., are also conventional cigarette additives. Furthermore, organic acids, which have significant influences on the flavour and taste of tobacco. are primary materials for the synthesis of higher aliphatic acids, amino acids and proteins in plants, Therefore, the analysis of inorganic anions and organic acids in tobacco are of great importance.

Recently, chloride ion, nitrate ion and nitrite ion in tobacco are generally determined by continuous flow analyzer in tobacco industry. Though traditional chemical analysis method is mostly employed for the determinations of fluoride ion, sulphate ion and the like, it has the disadvantages of complication, long time-consumption, low sensitivity and so on. Although the continuous flow analyzer method is widely applied, it could not be used for the simultaneous determinations of inorganic anions as described above. It has been reported in the domestic literature that inorganic anions in tobacco are simultaneously determined by means of ion chromatography. The classical organic acid determination method is to carry out gas chromatography analysis or gas chromatography-mass analysis after the esterifications of organic acids, but this method also have the disadvantages of long time-consumption, complication, high reagent-consumption and so on. It has also been reported that reverse phase high performance liquid chromatography and ion chromatography are employed to determine the organic acids in tobacco. Perini F R et al. employs ion chromatography to determine the carboxylic acids with low molecular weights such as formic acid, acetic acid, propionic acid, lactic acid and inorganic anions such as $F^-$, $Cl^-$, $NO_2^-$, $NO_3^-$ in tobacco products and auxiliary materials thereof. As reported in "Analysis of organic acids and inorganic anions in tobacco by ion chromatography and cluster analysis", *Acta Tabacaria Sinica*, 15 (4), August 2009, the contents of 9 organic acids and anions in tobacco sample are determined by ion chromatography, however, such technology would not be able to comprehensively and accurately determine the components in tobacco and even has the deficiency that some components would not be separated and thus the contents of components to be tested would be incorrectly obtained. Taking the separation between malonic acid and malic acid for example, said technology does not take the disturbance between the two components into consideration, malonic acid and malic acid in tobacco would be simultaneously eluted, the content of malonic acid would be mistakenly counted for the content of malic acid, leading to determination errors.

By now, it has not been reported that 16 inorganic anions and organic acids in tobacco could be quickly determined on the basis of sample injection for once.

SUMMARY OF THE INVENTION

The object of the present invention is to overcome the deficiencies of the prior reported methods, and to provide a sensitive, accurate, quick and convenient method for quick determination of 16 inorganic anions and organic acids in tobacco by one single time of injection.

The aforementioned object is achieved by the following technical solutions.

A method for quick and simultaneous determination of 16 inorganic anions and organic acids in tobacco, wherein a method of ion chromatography analysis is adopted. The elution process of said ion chromatography consist of:

| Time (min) | Concentration of KOH ($\rho$/mmol·$L^{-1}$) | Curve | Description |
|---|---|---|---|
| 0.000 | 1 | 5 | Start of analysis |
| 8.000 | 1 | 5 | Analysis of weak retaintion components |
| 28.000 | 30 | 5 | Analysis of medium retaintion components |
| 35.000 | 50 | 5 | Analysis of strong retaintion components |
| 40.000 | 50 | 5 | Purge system |
| 40.001 | 1 | 5 | Balance system |
| 50.000 | 1 | 5 | End of analysis |

The conditions of said ion chromatograghy consist of:
Conditions of Ion Chromatography:
(1) anion exchange column: IonPacAS11-HC (2 mm×50 mm)
   IonPacAG11-HC (2 mm×250 mm);
(2) column temperature: 30° C.;
(3) flow rate: 0.30 ml/min;
(4) injection volume: 25 μL;
(5) suppressor current: 50 mA.

The method for determination in present invention comprises the following steps:
(1) Standard stock solutions and the corresponding mixed standard solutions are prepared, and the detection limits of various components are determined according to the elution process and test conditions of the present invention;
Said standard stock solutions are standard solutions of fluoride ion, chloride ion, nitrite ion, bromide ion, nitrate ion, sulphate ion and phosphate ion (purchased from National Center of Standard Substances), the concentration of nitrite ion is 100 μg/mL, the concentrations of fluoride ion, chloride ion, nitrate ion, sulphate ion and phosphate ion are all 1000 µg/mL; the standard solutions of organic acid ions are prepared from guaranteed reagent of lithium lactate, sodium acette, sodium propionate, sodium formate, sodium butyrate, malic acid, malonic acid, citric acid and sodium oxalate (all purchased from Sigma-Aldrich Corporation). All organic acid ions are prepared as standard stock solutions at a concentration of 1000 µg/mL, stored at 4° C. in a refrigerator, and diluted to a series of mixed standard solutions, when using as required. Standard stock solutions are prepared with ultra-purified water (with the resistivity of 18.2 MΩ·cm), filtered through 0.45 µm microporous membrane, and then qualitatively analysed according to retaintion time. The linear regression equation and the coefficients of correlation coefficients of various components are obtained by quantitative analysis, i.e., external standard method of peak area. The detection limit of each component is determined at a signal-noise ratio of S/N=3.

(2) Pre-Treatment of the Testing Sample;

The tobacco sample to be tested is prepared into test sample according to the China Tabocco Industry Standard No. YC/T 31-1996, and then the water content is determined;

Said tobacco sample is ultrasonically extracted by ultra-purified water. The extract is filtered by qualitative filter papers, the first 2~3 mL of filtrate is discarded, and the subsequent filtrate is collected for further analysis;

(3) The filtrate is diluted to an appropriate concentration with purified water, filtered by 0.45 µm microporous membrane, and then analysed by ion chromatography according to said elution process and test conditions of the present invention;

(4) According to the peak areas, the ion concentrations of various organic acids or anions are calculated by via the linear regression equations.

The content equation of various organic acids or anions in tobacco is as follow:

$$m = c \cdot V \cdot 10^{-3} / W(1-x)$$

wherein c represents the ion concentration (mg/L); V represents the metered volume of the sample (mL); W represents the weight of powdered tobacco sample (g); x represents the water content of tobacco sample (%); m represents the amount of organic acid or anion per 1 g powdered tobacco sample (mg/g).

Compared with the prior reports, the present invention has the following beneficial effects:

Full-scale and accurate analysis of the components in tobacco is always regarded as the technical problem of this field. The key point with respect to simultaneous determinations of 16 components in tobacco lies in how to define the test conditions such as the best gradient elution process etc., on the basis of experiments. Just taking the gradient elution process for example, it requires higher performance of gradient elution process if there are more kinds of components to be determined. It requires that certain components with rather similar retention behaviours, e.g., some weak retention organic acids, could be accurately isolated within a reasonable analysis period. It is determined by the gradient elution process that whether the 16 components could be isolated to the extent of baseline separation without disturbance, so as to be quantitatively analysed accurately. On the basis of a large number of experiments, creative analysis and learnings, said gradient elution process as defined by the present invention, is found to be able to overcome the severe deficiencies in the prior art and make an important contribution to the determinations of tobacco components.

In addition, the chromatographic columns as used in the present invention, i.e., IonPacAS11-HC (2 mm×50 mm) and AG11-HC (2 mm×250 mm), have the inner diameter of 2 millimeters. Therefore, lower detection limits can be achieved. By further combining the other technical solutions as described in the present invention, the components which is of low concentration in tobacco, such as fluoride ion, nitrite ion, bromide ion, lactate ion, etc., could be simultaneously determined. As concluded in the experiment of the present invention, the flow rate of mobile phase of 0.30 mL/min is defined. By applying low mobile phase, The separation between different components to be tested is successfully improved.

Meanwhile, with respect to the pre-treatment of samples, differentiated from the prior art is that ultra-purified water is used for extraction in the present invention, rather than hydrochloric acid. Therefore, it is able to determine inorganic anions such as chloride ion in the samples, and further ensure the comprehensiveness and accuracy of the analysis results.

In conclusion, optimized gradient elution process and test conditions for ion chromatography are provided in the present invention, and a method for the simultaneous determinations of 16 inorganic anions and organic acids in tobacco by ion chromatography is defined, wherein said simultaneous determinations of inorganic anions such as $F^-$, $Cl^-$, $NO_2^-$, $Br^-$, $SO_4^-$, $NO_3^-PO_4^-$, and organic acids such as formic acid, acetic acid, propionic acid, propionic acid, lactic acid, malic acid, succinic acid, citric acid, oxalic acid, malonic acid, etc., in tobacco, are performed by one single time of sample injection. the advantage of this new method is that it is a rapid method with accurate result and convenient pre-treatments method. 16 kinds of inorganic anions and organic acids in tobacco can be simultaneously determined within 50 minutes. The difficulties of comprehensive and accurate analysis of components in tobacco are resolved. Therefore, it is of great importance in improving the inherent quality of tobacco and enhancing the quality control thereof.

DETAILED DESCRIPTION OF THE EMBODIMENTS

The present invention will be better understood on reading the following detailed description of nonlimiting embodiments thereof, and on examining the accompanying drawings.

Embodiment 1

Defining the Elution Process and the Analysis Conditions

In order to optimize the gradient elution process, the effect of different concentrations of sodium hydroxide solutions on the retaintion times of various components is studied in the experiment. Since there is a significant difference in the retaintion behaviours on chromatographic column between 16 inorganic anions and organic acid radical ions, the retaintion behaviours of weak retention components such as fluoride ion, lactic acid, acetic acid, propionic acid, formic acid and butyric acid are learned from the results of a great number of experiments of the present invention, as shown in FIG. 1.

Figure 1:
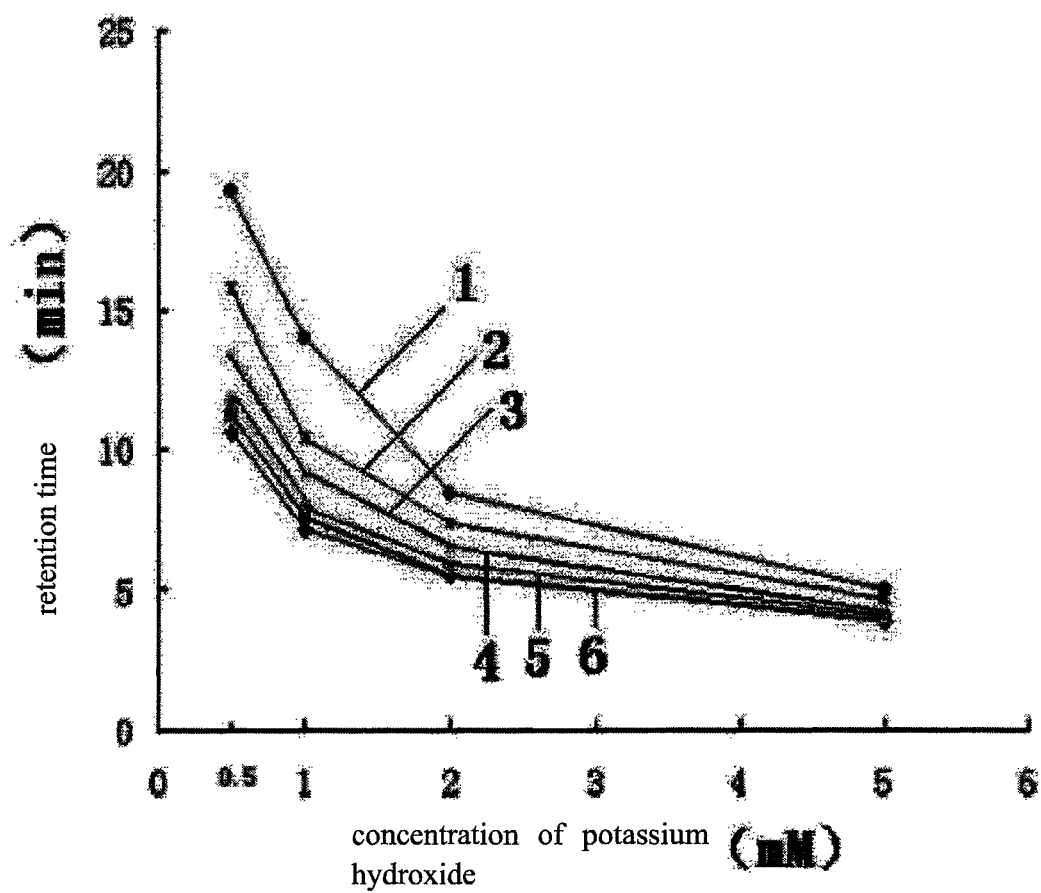
FIG. 1 refers to the effect of potassium hydroxide concentrations on the separations of weak retention components.

As shown in the curves in FIG. 1, at the order from top to bottom, 1 represents fluoride ion, 2 represents lactate ion, 3 represents acetate ion, 4 represents propionate ion, 5 represents formate ion, 6 represents butyrate ion. it could be concluded from FIG. 1 that for the elutions of weak retention components, relatively low concentration of KOH eluent is required in order to achieve a satisfactory separation result. Taking the separation between various components and the appropriate analysis time into comprehensive consideration, the initial KOH concentration of the gradient elution process is defined to be 1 mmol/L.

Figure 2:
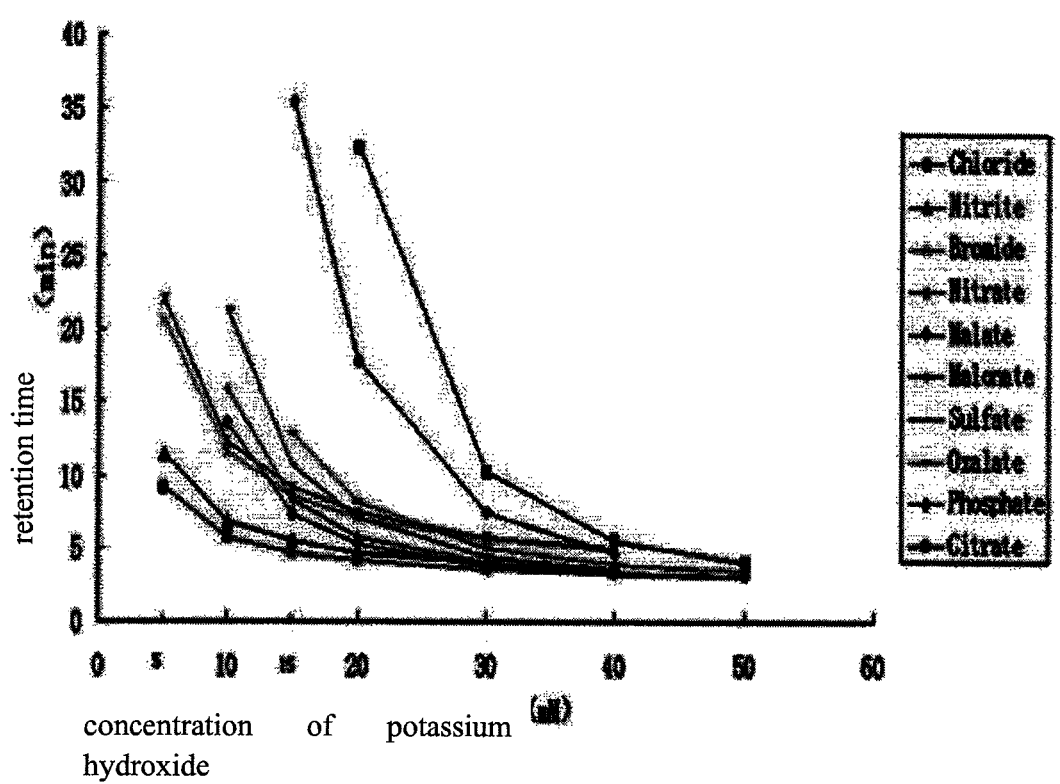
FIG. 2 refers to the effect of potassium hydroxide concentrations on the separations of medium and strong retention components.

For medium retention and strong retention ions, such as chloride ion, nitrite ion, bromide ion, nitrate ion, malate ion, malonate ion, sulphate ion, oxalate ion, phosphate ion, citrate ion, the effect of different potassium hydroxide concentrations on the retaintion times thereof are shown in FIG. 2. From FIG. 2, it could be concluded that for the elutions of medium and strong retentates, the concentration of KOH eluent should be appropriately increased. As concluded from the present invention, the concentration of KOH in eluent is increased from 1 mmol/L to 30 mmol/L during the period of 8 min~28 min of elution process, so as to quickly elute said strongly retained components off the column.

For phosphate ion and citric acid, the concentration of potassium hydroxide should be re-increased to 50 mmol/L, and the cleaning and the equilibrium of chromatography system are then performed. The elution process of the present invention are shown in Table 1.

TABLE 1

The gradient elution process for simultaneous ion chromatography analysis of inorganic anions and organic acids in tobacco

| Time (min) | Concentration of KOH (ρ/ mmol · L⁻¹) | | Curve Instruction |
|---|---|---|---|
| 0.000 | 1 | 5 | Start of analysis |
| 8.000 | 1 | 5 | Analysis of weak retention components |
| 28.000 | 30 | 5 | Analysis of medium retention components |
| 35.000 | 50 | 5 | Analysis of strong retention components retentate |
| 40.000 | 50 | 5 | purge system |
| 40.001 | 1 | 5 | balance system |
| 50.000 | 1 | 5 | End of Analysis |

Test Conditions of Ion Chromatography:
(1) anion exchange column: IonPacAS11-HC (2 mm×50 mm)
    IonPacAG11-HC (2 mm×250 mm);
(2) column temperature: 30° C.;
(3) flow rate: 0.30 ml/min;
(4) injection volume: 25 μL;
(5) suppressor current: 50 mA.

Embodiment 2

Determinations of Relative Standard Deviations (1) A series of corresponding mixed standard solutions are prepared from the stock solutions of various components, and ion chromatography analysis are performed according to said chromatographic conditions as described in Embodiment 1. Qualitative analysis is performed according to the retention times, the linear regression equation and the correlation coefficients of various components are obtained by quantitative method, i.e., external standard method of peak area. The detection limit of each component is determined at a Signa-noise ratio of S/N=3.

Said standard stock solutions are respective standard solutions of fluoride ion, chloride ion, nitrite ion, bromide ion, nitrate ion, sulphate ion and phosphate ion (all purchased from National Center of Standard Substances), the concentration of nitrite ion is 100 μg/mL, the concentrations of fluoride ion, chloride ion, nitrate ion, sulphate ion and phosphate ion are all 1000 μg/mL; the standard solutions of organic acid ions are uniformly prepared from guaranteed reagent of lithium lactate, sodium acetate, sodium propionate, sodium formate, sodium butyrate, malic acid, malonic acid, citric acid and sodium oxalate (all purchased from Sigma-Aldrich Corporation) at a concentration of 1000 μg/mL as standard stock solutions, stored at 4° C. in a refrigerator, and diluted to a series of mixed standard solutions, when using as required. Standard stock solutions are prepared with ultra-purified water (with the resistivity of 18.2 MΩ·cm), filtered through 0.45 μm micropour membrane, and then taken for determinations. Qualitative analysis is performed according to the retention times; the linear regression equations and the correlation coefficients of various components are obtained quantitative method, i.e., by external standard method of peak area. The detection limit of each component is determined at a signal-noise ratio of S/N=3. The standard regression equations, correlation coefficients and detection limits thereof are shown in Table 2.

TABLE 2

Standard regression equations, correlation coefficients and detection limits of anions and organic acids

| Component | Correlation coefficient r | Linear regression equation | Detection limit (ρ/μg · L⁻¹) |
|---|---|---|---|
| Fluoride ion | 0.9992 | A = 1.1329C − 0.0077 | 0.005 |
| Lactic acid | 0.9995 | A = 0.244C + 0.0019 | 0.021 |
| Acetic acid | 0.9996 | A = 0.2098C + 0.066 | 0.015 |
| Propionic acid | 0.9999 | A = 0.1558C + 0.0323 | 0.030 |
| Formic acid | 0.9986 | A = 0.3891C + 0.0412 | 0.013 |
| Butyric acid | 0.9998 | A = 0.1227C + 0.0114 | 0.025 |
| Chloride ion | 0.9991 | A = 0.6923C + 0.0757 | 0.005 |
| Nitrite ion | 0.9992 | A = 0.6144C − 0.0058 | 0.042 |
| Bromide ion | 0.9996 | A = 0.3018C − 0.0206 | 0.037 |
| Nitrate ion | 0.9994 | A = 0.3898C | 0.027 |
| Malic acid | 0.9999 | A = 0.1568C + 0.0278 | 0.018 |
| Malonic acid | 0.9990 | A = 0.2688C + 0.07 | 0.032 |
| Sulphate ion | 0.9995 | A = 0.5225C − 0.0547 | 0.016 |
| Oxalic acid | 0.9999 | A = 0.4747C + 0.0382 | 0.029 |
| Phosphoric acid | 0.9990 | A = 0.2181C − 0.0353 | 0.018 |
| Citric acid | 0.9996 | A = 0.1495C + 0.0594 | 0.065 |

According to the peak areas, the ion concentrations of various organic acids or anions are calculated by means of the linear regression equations.

The content equation of various organic acids or anions in tobacco is as follow:

$$m = c \cdot V \cdot 10^{-3} / W(1-x)$$

wherein c represents the ion concentration (mg/L); V represents the metered volume of sample (mL); W represents the weight of powdered tobacco sample (g); x represents the water content of tobacco sample (%); m represents the amount of organic acid or anion per 1 g powdered tobacco sample (mg/g).

(2) 0.5 g of a commercially available tobacco product is sampled and ultrasonically extracted by 50 mL of ultra-purified water for 25~40 min. The extract is filtered by qualitative filter paper, the first 2~3 mL of filtrate is discarded, and the subsequent filtrate is collected for further analysis. 10 mL of filtrate is transferred into a 100 mL volumetric flask and diluted with purified water to metered volume. The resulting solution is filtered by 0.45 μm micropore membrane, and analysed by ion chromatography according to the selected chromatographic conditions. Five repeated experiments are performed, and the relative standard deviations (RSD) thereof are calculated in accordance with the results of determinations, as shown in Table 3.

TABLE 3

The relative standard deviations of anions and organic acids

| Component | Fluoride ion | Lactic acid | Acetic acid | Propionic acid | Formic acid | Butyric acid |
|---|---|---|---|---|---|---|
| RSD (%) | 2.3 | 2.2 | 3.0 | 2.1 | 1.8 | 1.3 |
| Component | Chloride ion | Nitrite ion | Bromide ion | Nitrate ion | Malic acid | Malonic acid |
| RSD (%) | 0.6 | 1.1 | 0.9 | 1.2 | 0.7 | 1.3 |
| Component | Sulphate ion | Oxalic acid | Phosphoric acid | Citric acid | | |
| RSD (%) | 0.5 | 0.9 | 1.5 | 1.0 | | |

According to the results in Table 3, the relative standard deviations of organic acids and inorganic anions are in the range of 0.5% to 3.0%, which indicates that the method of the present invention is of good precision, and is able to meet the requirements of high standard analysis.

Example 3

Determination of Recovery 0.5 g of a commercially available tobacco product is ultrasonically extracted (with the ultrasonic power of 600 W) by 50 mL of ultra-purified water for 25~40 min, then 16 inorganic anions and organic acids of pre-know amount are respectively added thereinto. The contents are determined according to the above mentioned method. The recoveries thereof are calculated in accordance with the results of determinations, as shown in Table 4.

TABLE 4

The recoveries of anions and organic acids

| Component | Fluoride ion | Lactic acid | Acetic acid | Propionic acid | Formic acid | Butyric acid |
|---|---|---|---|---|---|---|
| Recovery (%) | 95.2 | 93.1 | 96.7 | 97.0 | 103.4 | 95.5 |
| Component | Chloride ion | Nitrite ion | Bromide ion | Nitrate ion | Malic acid | Malonic acid |
| Recovery (%) | 101.2 | 95.6 | 98.5 | 97.2 | 102.6 | 94.6 |
| Component | Sulphate ion | Oxalic acid | Phosphoric acid | Citric acid | | |
| Recovery (%) | 100.8 | 97.4 | 103.1 | 95.1 | | |

According to the results in Table 4, the recoveries of organic acids and inorganic anions are in the range of 93.1% to 103.4%, which indicates that this method is accurate, and is able to meet the requirements of high standard analysis, so as to be used for accurate quantitative analysis.

What is claimed is:

1. A method for quick and simultaneous determination of 16 inorganic anions and organic acids in tobacco by ion chromatography, wherein the elution process comprises:

analysing filtrates extracted from a tobacco sample in accordance with the following elution process and conditions;

| Time (min) | Concentration of KOH (ρ/mmol·L$^{-1}$) | Curve | Description |
|---|---|---|---|
| 0.000 | 1 | 5 | Start of analysis |
| 8.000 | 1 | 5 | Analysis of weak retention components |
| 28.000 | 30 | 5 | Analysis of medium retention components |
| 35.000 | 50 | 5 | Analysis of strong retention components |
| 40.000 | 50 | 5 | Purge system |
| 40.001 | 1 | 5 | Balance system |
| 50.000 | 1 | 5 | End of analysis | conditions of said ion chromatograghy being: anion exchange column: IonPacAS11-HC (2 mm×50 mm) and IonPacAG11-HC (2 mm×250 mm); column temperature: 30° C.; flow rate: 0.30 ml/min; injection volume: 25 μL; suppressor current: 50 mA; and wherein the method further comprises steps for pre-treating the tobacco sample before analysis, the steps for pre-treating the tobacco sample consisting of:

(1) determining the percentage of moisture in the tobacco sample;

(2) pre-treating the tobacco sample by extracting the tobacco sample ultrasonically by extraultra-purified water at a ratio of 1 g tobacco sample: 10 mL water and then filtering the sample to collect the filtrates; and (3) diluting the filtrates tenfold and then filtering the filtrates.

2. The method according to claim 1, wherein the inorganic anions and organic acids are selected from the group consisting of fluoride ion, bromide ion, chloride ion, nitrate ion, nitrite ion, sulphate ion, phosphate ion, lactic acid, malic acid, citric acid, oxalic acid, formic acid, acetic acid, propionic acid, butyric acid, and malonic acid.

* * * * *